(12) United States Patent
Edwards et al.

(10) Patent No.: US 11,325,103 B2
(45) Date of Patent: May 10, 2022

(54) TEMPORARY HYDROPHOBIC MATRIX MATERIAL TREATMENTS, MATERIALS, KITS, AND METHODS

(71) Applicant: LIA DIAGNOSTICS, INC., Philadelphia, PA (US)

(72) Inventors: Bethany Edwards, Philadelphia, PA (US); Anna Couturier, Philadelphia, PA (US)

(73) Assignee: LIA DIAGNOSTICS, INC., Philadelphia, PA (US)

(*) Notice: Subject to any disclaimer, the term of this patent is extended or adjusted under 35 U.S.C. 154(b) by 0 days.

(21) Appl. No.: 16/318,097

(22) PCT Filed: Jul. 14, 2017

(86) PCT No.: PCT/US2017/042239
§ 371 (c)(1),
(2) Date: Jan. 15, 2019

(87) PCT Pub. No.: WO2018/013986
PCT Pub. Date: Jan. 18, 2018

(65) Prior Publication Data
US 2021/0060529 A1 Mar. 4, 2021

Related U.S. Application Data

(60) Provisional application No. 62/362,813, filed on Jul. 15, 2016.

(51) Int. Cl.
*B01J 20/28* (2006.01)
*B01J 20/10* (2006.01)
*B01J 20/24* (2006.01)

(52) U.S. Cl.
CPC .......... *B01J 20/2803* (2013.01); *B01J 20/103* (2013.01); *B01J 20/24* (2013.01); *B01J 20/28023* (2013.01); *B01J 20/28035* (2013.01)

(58) Field of Classification Search
CPC ...... B01J 20/28; B01J 20/2803; B01J 20/103; B01J 20/24; B01J 20/28023; B01J 20/28035
USPC ....................................................... 502/404
See application file for complete search history.

(56) References Cited

U.S. PATENT DOCUMENTS

| | | |
|---|---|---|
| 5,246,664 A | 9/1993 | Nagata et al. |
| 5,378,638 A | 1/1995 | Deeg et al. |
| 5,509,913 A | 4/1996 | Yeo |
| 5,552,288 A | 9/1996 | Christensen et al. |
| 6,403,298 B1 | 6/2002 | Lee et al. |
| 6,808,598 B1 | 10/2004 | Takeuchi et al. |
| 10,045,694 B2 | 8/2018 | Edwards et al. |
| 10,542,886 B2 | 1/2020 | Edwards et al. |
| 2005/0131362 A1 | 6/2005 | Przepasniak et al. |
| 2008/0299005 A1 | 4/2008 | Meathrel et al. |
| 2008/0286879 A1 | 11/2008 | Lee |
| 2009/0054548 A1 | 2/2009 | Wang et al. |
| 2009/0263854 A1 | 10/2009 | Jacono et al. |
| 2009/0264836 A1 | 10/2009 | Roe et al. |
| 2011/0105360 A1 | 5/2011 | Derda et al. |
| 2012/0072125 A1 | 3/2012 | Sharrock |
| 2012/0130331 A1 | 5/2012 | Wang et al. |
| 2013/0109837 A1 | 5/2013 | Bhandari et al. |

FOREIGN PATENT DOCUMENTS

| | | |
|---|---|---|
| CN | 1208088 A | 2/1999 |
| CN | 1658902 A | 8/2005 |
| CN | 102099678 A | 6/2011 |
| CN | 102735835 A | 10/2012 |
| CN | 204241487 U | 4/2015 |
| EP | 0801172 A1 | 10/1997 |
| JP | S6224145 A | 2/1987 |
| JP | H03162956 A | 7/1991 |
| JP | H0523716 B2 | 4/1993 |
| JP | H5149946 A | 6/1993 |
| JP | H0616043 B2 | 3/1994 |
| JP | H06201690 A | 7/1994 |
| JP | 2001115368 A | 4/2001 |
| JP | 2007513345 A | 5/2007 |
| JP | 2011183613 A | 9/2011 |
| WO | 9508761 A1 | 3/1995 |
| WO | 1997013920 A1 | 4/1997 |
| WO | 9808475 A1 | 3/1998 |
| WO | 2005054845 A1 | 6/2005 |
| WO | 2011018618 A2 | 2/2011 |
| WO | 2015175301 A1 | 5/2014 |
| WO | 2015181056 A1 | 12/2015 |

OTHER PUBLICATIONS

Zhihua Zhang et al, "Hydrophobic Silica Aerogels Strengthened with Nonwoven Fibers", Journal of Macromolecular Science, Part A—Pure and Applied Chemistry, Feb. 7, 2007, pp. 1663-1670, vol. 43, No. 11, US.

Fortea-Verdejo Marta et al, "Upgrading flax nonwovens: Nanocellulose as binder to produce rigid and robust flax fibre preforms", Composites Part A: Applied Science and Manufacturing, Elsevier, Nov. 17, 2015, pp. 63-71, vol. 83, Amsterdam, NL.

Wang et al., "Monitoring the Disease Activity via the Antibody-Antigen Recognition in Paper", Nano/Micro Engineered and Molecular Systems (NEMS), 2013 8th IEEE International Conference on (pp. 229-232).

Anonymous, "LIA—IPD: Integrated Product Design", Integrated Product Design Program, University of Pennsylvania, PA, USA, URL: https://ipd.me.upenn.edu/portfolio/lia/, retrieved on Nov. 15, 2018.

(Continued)

*Primary Examiner* — Edward M Johnson
(74) *Attorney, Agent, or Firm* — Rimôn, P.C.

(57) ABSTRACT

Herein provided are treated matrix materials including a binding agent and a hydrophobic nanoparticle treatment that are formed or formable into water dispersible or biodegradable products, including manufacturing methods therefore.

15 Claims, 1 Drawing Sheet

(56) References Cited

OTHER PUBLICATIONS

John Paul Titlow, "The Pregnancy Test Of The Future Is Flushable, Private, And Sustainable", Fast Company, URL: hllps://www.fastcompany.com/3047152/the-pregnancy-test-of-the-future-is-flushable-private-and-sustainable, retrieved on Nov. 16, 2018.

EMD Millipore, "Performance of Estapor Microspheres and Hi-Flow(TM) Plus Membranes in a Lateral Flow Assay or Human Chorionic Gonadotropin (hCG) EMD Millipore (Application Note)", URL: htttps://www.emdmillipore.com, retrieved on Nov. 16, 2018.

TEMPORARY HYDROPHOBIC MATRIX MATERIAL TREATMENTS, MATERIALS, KITS, AND METHODS

CROSS-REFERENCE TO RELATED APPLICATIONS

This application is a United States national stage entry of International Application serial no. PCT/US2017/042239 filed Jul. 14, 2017 which claims priority to U.S. Provisional Application Ser. No. 62/362,813 filed Jul. 15, 2016. The contents of these applications are incorporated herein by reference in their entirety.

BACKGROUND

Cellulosic nonwoven materials are absorbent, non-rigid, and disperse quickly when exposed to a solution such as water. The inventors have identified a need to adapt these and similar dispersible, dissolvable or biodegradable materials to provide, for example, temporary hydrophobicity so a cellulosic material will initially repel water and hold structure, but over time will absorb water and disperse when submerged. However, coatings on such materials can vary the stiffness, hydrophobicity, and dispersion characteristics of the resulting or coated material. The solutions presented herein address these and other needs in the art.

SUMMARY

In certain frequent embodiments, a water dispersible and/or biodegradable (optionally non-woven) matrix material is provided comprising a binding agent and a hydrophobic nanoparticle coating.

Also in frequent embodiments, a (optionally non-woven) matrix coating solution is provided comprising a binding agent, a hydrophobic nanoparticle coating, and deionized water.

In certain frequent embodiments, a water dispersible and/or biodegradable (optionally non-woven) matrix material is provided comprising an exposed surface and wherein a contact angle of the exposed surface is greater than 90°.

In certain embodiments, the (optionally non-woven) matrix material is comprised of a plurality of fibers and at least one of the plurality of fibers is coated with the hydrophobic nanoparticle.

In frequent embodiments, the (optionally non-woven) matrix material is comprised of a plurality of fibers and at least one of the plurality of fibers is coated with the binding agent and the hydrophobic nanoparticle. Also frequently, the (optionally non-woven) matrix material comprises a water dispersible and/or biodegradable matrix material. Often, the water dispersible and/or biodegradable matrix material is selected from one or more of the group comprising HYDRASPUN® (Suominen Corporation PLC, FINLAND), HYDRASPUN PLUS, SOFTFLUSH, NBOND, or other cellulosic nonwoven material.

In frequent embodiments, the binding agent comprises a soluble carbohydrate material such as a starch. Also, in certain embodiments, the binding agent comprises a gelatin, silk, or soy. In certain embodiments, the binding agent comprises another soluble polymer such as polyvinyl alcohol (PVA), polyacrylic acid (PAA), a water soluble polyacrylamide, xanthum gum, pectin, chitosan, dextran, cellulose, and/or derivative thereof. Also frequently, the hydrophobic nanoparticle comprises silicon dioxide, for example, non-fluoronated silicon dioxide. In certain embodiments, the hydrophobic nanoparticle comprises a styrene particle such as manganese oxide polystyrene, zinc oxide polystyrene, etc. Also in certain embodiments, the hydrophobic nanoparticle comprises calcium carbonate. Also in certain embodiments, the hydrophobic nanoparticle comprises a silica nano-coating.

In certain frequent embodiments, the binding agent comprises a starch and the hydrophobic nanoparticle comprises silicon dioxide and the water dispersible and/or biodegradable matrix material is selected from one or more of the group comprising HYDRASPUN, HYDRASPUN Plus, HYDRASPUN Essential, SOFTFLUSH, and NBOND.

Often, the water dispersible and/or biodegradable (optionally non-woven) matrix material comprises multiple layers, and wherein each layer of the multiple layers is adhered to another layer of the multiple layers with a binding agent that dissolves in water. In certain embodiments, the (optionally non-woven) matrix material comprises multiple layers, and wherein each layer of the multiple layers is attached to another layer of the multiple layers using stapleless attachment.

In frequent embodiments, the contact angle is at or about 150°. Also frequently, the contact angle is between 90° and 180°. In often included embodiments, the contact angle is between 90° and 150°.

In frequent embodiments, the (optionally non-woven) matrix material includes a perforation adapted to permit liquid to pass through the hydrophobic nanoparticle coating to the matrix material.

In often included embodiments, the matrix material disperses in water when exposed to the water for over 1 minute.

The water dispersible and/or biodegradable (optionally non-woven) matrix material also frequently comprises a flushable consumer product. Often the consumer product comprises a diagnostic test, a packaging, instructions, a waste disposal device, a product mold, a container, a housing, or a tablet.

Methods are also provided, including a method of forming a rigid water dispersible and/or biodegradable (optionally non-woven) matrix material comprising contacting the water dispersible and/or biodegradable (optionally non-woven) matrix material with matrix coating solution to created a treated matrix material and drying the treated matrix material to form the rigid water dispersible and/or biodegradable (optionally non-woven) matrix material. The contacting of the solution often contacting comprises submersing or spraying the matrix material, a gravure roll/cylinder, slot coating the matrix material, immersing material and excess solution is squeezed off with rollers (i.e., dip and nip) or other methods. In often included embodiments, the formed rigid water dispersible and/or biodegradable (optionally non-woven) matrix material comprises an exposed surface and wherein a contact angle of the exposed surface is greater than 90°.

Methods of forming a rigid water dispersible and/or biodegradable (optionally non-woven) matrix material containing multiple layers of the (optionally non-woven) matrix material are also provided, for example, comprising contacting each of the multiple layers with one-another, and contacting one or more layer of the multiple layers with the solution of claim 8 to created a treated multi-layer matrix material and drying the treated multi-layer matrix material to form the rigid water dispersible and/or biodegradable (optionally non-woven) matrix material. In often included embodiments, the formed rigid multi-layer water dispersible and/or biodegradable (optionally non-woven) matrix material comprises an exposed surface and wherein a contact angle of the exposed surface is greater than 90°.

The one or more layers of the multiple layers is often contacted with the solution prior to contacting each of the multiple layers with one-another. Alternatively, the one or more layers of the multiple layers is may be often contacted with the solution after contacting each of the multiple layers with one-another.

In certain embodiments, a temporary membrane backing is provided to the matrix material. Often in such embodiments, an application of a hydrophobic nanoparticle is provided to the matrix material and permitted to penetrate at least a portion of the matrix material (e.g., 20% to about 80%), often at or about 50% of the matrix material. In certain embodiments a reagent is applied to the matrix material containing a temporary membrane backing.

In certain embodiments, a kit is provided comprising a (optionally non-woven) matrix material and a hydrophobic nanoparticle.

These and other embodiments, features, and advantages will become apparent to those skilled in the art when taken with reference to the following more detailed description of various exemplary embodiments of the present disclosure in conjunction with the accompanying drawings.

BRIEF DESCRIPTION OF THE DRAWINGS

The skilled person in the art will understand that the drawings, described below, are for illustration purposes only.

DETAILED DESCRIPTION OF THE VARIOUS EMBODIMENTS

Figure 1:
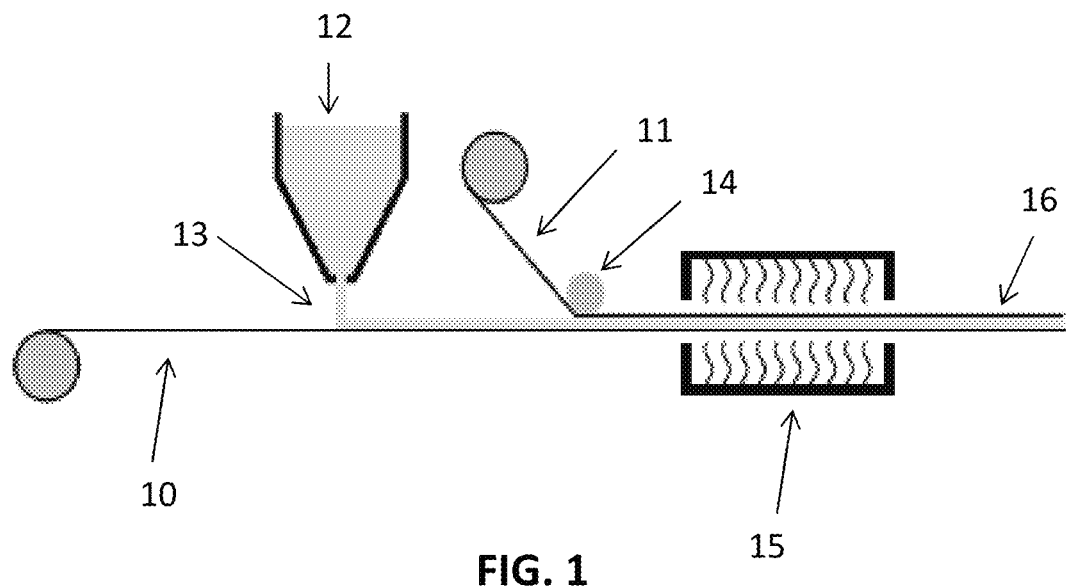
FIG. 1 depicts an exemplary lamination workflow diagram.

For clarity of disclosure, and not by way of limitation, the detailed description of the various embodiments is divided into certain subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, the term "dispersible" means that the fibers or chunks of a material are capable of debonding or separating, resulting in the material breaking down into smaller pieces than the original sheet. Debonding is generally a physical change of scattering or separation, as compared to a state change, such as dissolving, wherein the material goes into solution, e.g., a water soluble polymer dissolving in water. For clarity, a material may be dispersible when broken down into smaller clumps of the larger material without fibers dispersing.

As used herein, the term "soluble" has a conventional meaning. In other words, "soluble" refers to the ability of a specified material to dissolve in another substance such as water, a fluid sample, or another fluid.

As used herein, the phrase "fibrous nonwoven composite structure" refers to a structure of individual fibers or filaments with or without particulates which are interlaid, but not in an identifiable repeating manner. Nonwoven structures such as, for example, fibrous nonwoven webs have been formed in the past, by a variety of processes known to those skilled in the art including, for example, meltblowing and meltspinning processes, spunbonding processes, bonded carded web processes, hydroentangling, pressing, electrospinning, and the like. Such structure is often referred to generally herein as "non-woven" or "non-woven matrix."

As used herein, the phrase "matrix material" includes water soluble, water dispersible, biodegradable, compostable, and/or flushable material. The matrix material may comprise a nonwoven structure, a porous structure, semiporous structure, gel, a solid, a semi-solid, or other structure.

As used herein, the phrase "water dispersible" refers to a material (often nonwoven and fibrous) that, when placed in an aqueous environment will (over time) break apart into smaller pieces or fibers. Once the structure is broken apart and dispersed, it is processable in recycling processes, for example, septic and municipal sewage treatment systems. If desired, the fibrous nonwoven structures can be made more water-dispersible or the dispersion can be quickened. The actual amount of time for dispersion can vary and be predetermined based on the intended use profile. A water dispersible material may also be biodegradable.

As used herein, "biodegradable" refers to a material that is capable of being decomposed by bacteria or other living organisms, natural processes, or other biological agents or means. A biodegradable material may also be water dispersible.

As used herein, "flushable" refers to materials that pass the flushablity guidelines of IVDA and/or EDANA, for example, as set forth in the current "Guidelines for Assessing the Flushability of Disposable Nonwoven Products," Third Edition, August 2013, IVDA and EDANA, or another current industry accepted flushability standard, guideline, recommendation, requirement, or objective.

As used herein, "absorbent" refers to the capacity or tendency to absorb a fluid. Though not wishing to be bound by any particular theory, absorbent materials have a tendency to resist wicking of fluids therethrough.

As used herein, "rigid" refers to an ability to hold form without deformation, bending, creasing or otherwise being forced out of shape. A rigid material may be formable such that can be manipulated to form a shape (e.g., when wetted) and this shape is resistant to deformation under certain conditions (e.g., when dried). A rigid material may have some low degree of flexibility over a given length, depending on the applied force. A rigid material may have varying degrees of rigidity.

As used herein, "nanoparticle" is used as a descriptor without limitation to the actual physical dimensions of the underlying molecular or chemical moiety or particle. As such and for example, a nanoparticle such as a hydrophobic nanoparticle may be measurable on the micro and nano scales. References to a "hydrophobic nanoparticle" herein specifically include hydrophobic coatings or hydrophobic solutions containing, e.g., a hydrophobic nanoparticle, unless specifically defined otherwise. Non-limiting exemplary hydrophobic nanoparticles include silicon dioxide, non-fluoronated silicon dioxide, calcium carbonate, silica nano-coating, and styrene particles such as manganese oxide polystyrene, zinc oxide polystyrene, etc. For clarity, silicon dioxide is meant to refer to fluorinated and non-fluorinated forms.

Other features and advantages of the disclosure will be apparent from the following description and referenced drawings. The present innovations are often further described by exemplary embodiments. The examples are provided solely to illustrate the innovations by reference to specific embodiments. The drawings, which are not necessarily to scale, depict selected embodiments and are not intended to limit the scope of the present disclosure. These exemplifications, while illustrating certain specific aspects of the innovations, do not portray the limitations or circumscribe the scope of the disclosed innovations. The detailed description illustrates by way of example, and is not intended to limit the scope of the present disclosure.

The water dispersible or soluble matrix materials contemplated herein provide, for example, a seamless and environmentally sustainable manufacturing process and use protocol. In particular, in frequent embodiments, a water dispersible or soluble matrix material is utilized to constitute multiple components/aspects of the contemplated devices.

One exemplary material contemplated herein as a water dispersible matrix is a nonwoven fabric material called HYDRASPUN®, or its related products. Though not wishing to be bound by any particular theory of operation, characteristics of this material that are utilized in the presently contemplated methods and devices are an increased resistance to water-dispersion. In other words, this material is and can be characterized as absorbent. In certain embodiments, the nonwoven fabric material comprises water content of less than about 10% by weight. In certain embodiments, the water dispersible or soluble matrix material comprises a dry tri-layered material having an internal layer of, for example, cellulose pulp fibers, an upper layer of said continuous filaments of a water-soluble or water-dispersible polymer and a lower layer of said continuous filaments of a water-soluble or water-dispersible polymer. Other water dispersible or soluble matrix materials are contemplated and described, for example, in U.S. Pat. Nos. 4,309,469, 4,419,403, 5,952,251, and/or 8,668,808. SOFTFLUSH® (Jacob Holm & Sons AG) and NBOND® (Hangzhou Nbond Nonwoven Co., Ltd. Corp.) are additional examples of water dispersible and/or biodegradable matrix materials.

As used herein, the term "matrix material" (including non-synthetic matrix material, water dispersible or soluble matrix material, water dispersible matrix sandwich material, etc.) excludes nitrocellulose and nitrocellulose material. Most frequently, this matrix material comprises a flushable, water dispersible, biodegradable, and/or soluble matrix material such as a nonwoven web material. The term "matrix material" is also intended to refer to the material regardless of whether it has been treated with a coating or lamination.

As noted, the flushable or water dispersible nonwoven materials contemplated herein for use as assay devices or device components are generally absorbent materials. Moreover, such materials also often lack sufficient rigidity to withstand typical use conditions (e.g., using as a mid-stream device) without having to orient them in a specific manner, often using a support. Conversely, when such materials are supported with other materials (e.g., sandwiched materials, laminates, or coatings) those materials often interfere with the ability of the device to become wetted sufficient to initiate dispersion. For example, the materials may cause the device to float on the water surface for an extended time due to the added time it takes for water to pass into or across the laminate or coating to initiate dispersion. The drawbacks to such delayed dispersion are significant, including the inability to pass flushability standards.

As such, improved methods of and materials for strengthening nonwoven materials, such as those contemplated herein, while permitting water dispersion are contemplated and described herein. For example, a technique is provided that creates a temporary hydrophobic aqueous coating, for both binding and lamination, suitable for strengthening a nonwoven, while also allowing it to ultimately, disperse in water. The aqueous solution or coating often serves as a temporary hydrophobic barrier, and also frequently as a binding agent. Multiple layers of a nonwoven material, for example a cellulosic nonwoven (e.g., 80% cellulose, 20% rayon or lyocell), can be secured together, for an extended duration, allowing for various uses, with only the application of an aqueous coating/submersion and pressure.

In certain embodiments non-adhesive attachment is provided between multiple layers of a non-woven matrix material. Stapleless attachment using, for example, attachment means provided by stapleless stapling technology is employed as one exemplary embodiment to combine or attach multiple layers of a non-woven matrix material without adhesive. One exemple of stapleless stapling technology is the Harinacs stapler available from Kokuyo Co. Ltd. (Higashinari-ku, Osaka, Japan), or similar. Such staplers operate on a relatively small scale and are provided for general reference only to stapleless attachment technology, but reference thereto is intended to be non-limiting other than it refers to matrix layer attachment without staples (including other added mechanical attachments) or adhesive. Stapleless attachment technology is specifically contemplated herein as scalable to large scale and/or continuous manufacture through, for example, stamping and roll-to-roll operations. For simplicity, such technology is referred to herein as a stapleless stapler or stapleless attachment. Though not wishing to be bound by any particular theory of operation, a stapleless stapler acts to use the nature of the non-woven fabric to combine with itself without introducing any foreign bodies to the matrix. In this regard, mini folds or post-wet-laid interactions of the fibers of the non-woven matrix fabric are introduced between two or more layers of the matrix material to combine/attach the layers in a manner similar to being stapled together. This technique is often employed to attach two layers of a matrix material that have been, or will be, treated with a hydrophobic nanoparticle as described herein. In such embodiments a fully flushable or otherwise environmentally friendly housing or structure is created using simply the matrix material itself. While this technique is well situated for water dispersible products as they stand alone, the inventors have found this technique to be readily adaptable to the commercial manufacture of water dispersible products that require or benefit from the combination of multiple layers of water dispersible matrix material.

Existing methods focus on creating a superhydrophobic barrier. These types of barriers and the chemical compounds required to achieve them, render them unable to disperse in water and/or pass flushability guidelines. In fact, innovation in this general technical area is skewed toward completely opposed areas: (1) no barriers, quick dissolving barriers, or barriers that breakdown quickly when exposed to a liquid (e.g., MonoSol, etc.); or (2) those that are designed to repel liquid and not breakdown (e.g., absorbent nonwovens used in diapers). While some wetlaid, cellulosic nonwovens are designed to be both absorbent and flushable, they are fabric-like, lacking the rigidity or strength to retain a dimensional form. The coating and lamination process presented transforms the flexible, water-dispersible nonwoven into a material capable of holding and forming dimension. Additionally, nonwovens are generally regarded as unable to pass flushability tests and standards. If flushability is also desired, then an additional challenge associated with sink testing arises. The presently described innovations address these challenges.

Coated matrix materials of the present disclosure in certain embodiments include physical manipulations of the material to enhance dissolution in water. In such embodiments, a perforation such as a partial perforation, or perforation line, in the matrix material is provided. Often the perforation or score line is adapted to define a fold or crease line created when the device is exposed to water and optionally agitated. A perforation is most frequently provided after deposition of a hydrophobic nanoparticle. In certain embodiments, such a perforation or perforation line is introduced to the device after use. In certain related embodiments, the device is folded or manipulated by a user to introduce the perforation or perforation line. Though not wishing to be bound by any particular theory, the perforation through the hydrophobic nanoparticle provides a break in the resulting coating that permits the more rapid entry of water or other dissolution solution (when exposed) to the matrix material at the point of perforation. This more rapid entry of water or other dissolution solution provides for the initiation of the breakdown of the matrix at the point of perforation in advance of portions of the matrix that are treated with the hydrophobic nanoparticle. This more rapid entry of water results in a weakening of the matrix at the point of the perforation to permit folding of the matrix at that point. For clarity, a fold in this context includes a more flexible area, a bend or other area of reduced or weakened structural integrity of the matrix upon an initial exposure to water. While the entirety of the matrix will become wetted and weakened, the perforation permits a more rapid weakening at the point of the perforation. Often the perforation is provided in the form of a perforation line or multiple perforation lines in the matrix material. A perforation line is provided in a manner suitable to the intended use of the matrix. For example, in the embodiment of a diagnostic intended to be flushed in a toilet, the line of perforation (including one or more or plurality of lines of perforation) may be provided to enhance the flushability of the matrix. The configuration of this line of perforation often will result in one or multiple folds in the matrix to reduce the overall size of the matrix relative to its pre-folded state.

An exemplary aqueous coating/lamination solution comprises a mixture of a strengthening and binding agent (e.g., starch or another water soluble polymer), a hydrophobic nanoparticle (e.g., silicon dioxide, TiO2, Silver nanoparticles, other metal oxides, among others.), and deionized (DI) water. Deionized water may be substituted with another suitable solvent, which solvent is often capable of average to rapid evaporation when exposed to certain environmental conditions such as ethanol or other alcohols. When making the solution, a nanoparticle dispersion is, for example, mixed into a starch solution at a predetermined dilution. The binding agent and nanoparticles bind to the fibers of the matrix material, when applied. Though not seeking to be bound by any particular theory of operation, the materials fill spaces in the matrix material. The binding agent, for example, binds and stiffens the fibers in the matrix material; and the nanoparticles (e.g., SiO2) alter the surface tension around the matrix material and making the resulting material much "rougher" at a nanoscale. This change in the nanotexture acts to increase the contact angle of water/liquids when they come in contact with the matrix material. The most frequent embodiments include aqueous coating/lamination solutions having nanoparticles (and/or other ingredients) that are environmentally friendly, biodegradable, or have a Generally Recognized as Safe (GRAS) designation with the American Food and Drug Administration, European Commission, or the European Food Safety Authority.

The contact angle is the angle, conventionally measured through the liquid, where a liquid—vapor interface meets a solid surface. It quantifies the wettability of a solid surface by a liquid via the Young equation. In general, nanoparticle solutions or coatings that increase the contact angle are contemplated for use herein together with the contemplated matrix materials. In certain frequent embodiments, the coating/lamination solution provides a contact angle of at or about 150°. Often, the coating/lamination solution provides a contact angle that is characterized as superhydrophobic, for example, at 150° or greater. Also often, the coating/lamination solution provides a contact angle that is characterized as superhydrophobic, for example, at between 90° and 150°. The matrix may comprise all or a portion of fibers that have contact angles of greater than 90° on at least a portion of their surface. In certain embodiments, the matrix comprises fibers, a portion of which being characterized as hydrophobic or superhydrophobic, and another portion of the fibers being characterized as hydrophilic.

In practice, once the Aqueous Coating/Solution is mixed, the lamination process is performed by, for example: Spray deposition, submersion, or roll lamination. In one exemplary manufacturing process, the absorbency properties of the matrix material combined with the solution allow the matrix material layers to bind together using pressure alone, without the need for additional adhesives or heat application to obtain adherence. In general a matrix material treated with a coating/lamination solution described herein is considered to be a treated matrix or treated matrix material.

The submersion method involves stacking layers or sheets of a matrix material and submerging them into an exemplary coating/lamination solution, followed by curing. In one exemplary process, the following steps are employed:
1) Solution is mixed;
2) At least one web of wetlaid cellulosic nonwoven is/are aligned and submerged into solution;
3) The web/webs of nonwoven material is/are removed from the solution and excess solution is removed, e.g., via squeegee;
4) The now laminated material is permitted to dry;
   a) 24 hour ambient cure time; or
   b) Drying can optionally be accelerated using elevated temperatures, e.g., up to 150° C.

Roll lamination may be also employed to impregnate matrix material with coating/lamination solution. In one exemplary process, roll-to-roll lamination is performed utilizing a machine, such as the Labline (e.g., model 750 or 800, available from GeMaTa Spa Division Ro Trissino, IT), Kinematic Matrix 6500, IMS Microwave dryer, infrared dryer, or similar machine. In general, the process involves aqueous coating and laminating, roll-to-roll. In one exemplary process, the following steps are employed:
1) Solution is mixed;
2) Machine is threaded and setup to allow for two layers, or any desired number (1+), of the nonwoven;

3) The webs of the nonwoven come in contact;
   a) (Aqueous) coating applied by any of the following: immersion/dip, knife, gravure roll/cylinder, spray, slot coating, printing; or
   b) The webs are coated individually then brought together to dry;
4) The now laminated material is left to dry;
   a) The web is sent through an accelerated drying oven under temperatures up to 150° C.; or
   b) 24 hour ambient cure time FIG. 1 depicts one exemplary lamination process involving depositing (13) a coating solution (12) to a first matrix material (10), contacting an additional matrix material (11) with the coated first matrix material using a roller, drying the contacted matrix materials using a heat source (15) to create a coated matrix material (16). The coating solution often comprises a hydrophobic nanoparticle solution. The coated matrix material (16) comprises a nanolayer coating.

Figure 2:
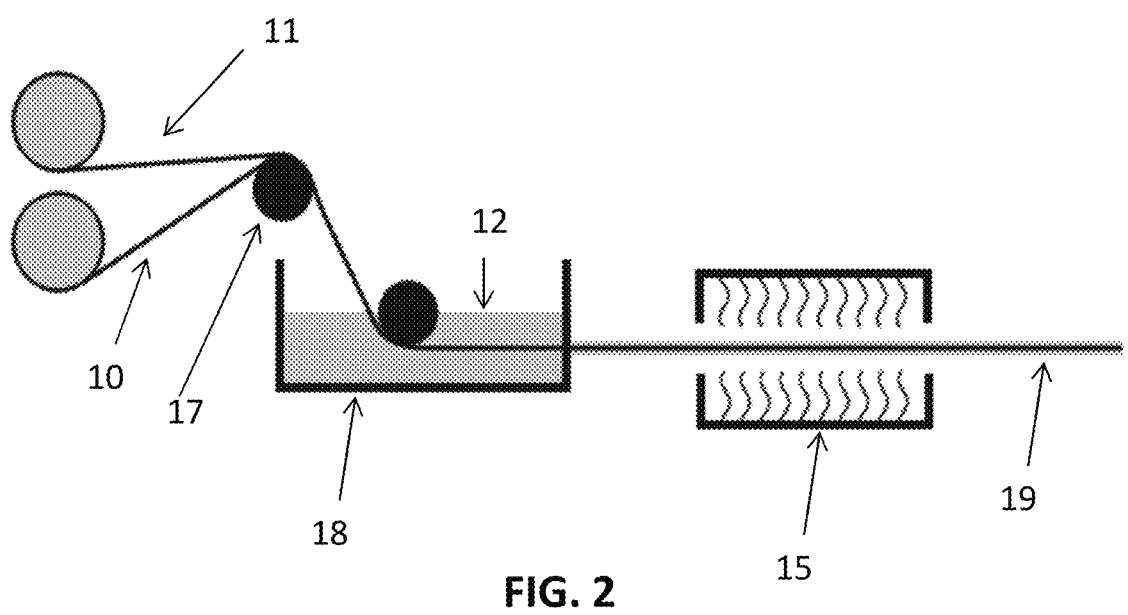
FIG. 2 depicts another exemplary lamination workflow diagram.

FIG. 2 depicts another exemplary lamination process involving contacting a first matrix material (10) with an additional matrix material (11), submersing the contacted matrix materials in a coating solution (12), drying the contacted matrix materials using a heat source (15) to create a coated matrix material (19). The coating solution often comprises a hydrophobic nanoparticle solution. The coated matrix material (19) comprises a nanolayer coating.

In certain embodiments, the above process is adapted to prepare the matrix and assemble devices in a continuous manufacturing line, including other process steps (which may or may not be optional steps) such as matrix cutting or adaptation, embossing, further treatment of matrix material to increase reagent (e.g., antibody) binding affinity, further treatment to increase or enhance sinkability, and/or reagent application/integration.

In certain embodiments, the matrix material is a single, non-layered, material. In such embodiments, the matrix material has an increased thickness that is similarly treated via submersion, roll lamination or another method. Also in certain embodiments, multiple different matrix materials are laminated and bound together. In such embodiments, the different matrix materials can be separately laminated or laminated together via submersion, roll lamination or another method.

It is also contemplated that a matrix material comprised of pre-treated fibers is utilized. In such an embodiment, the fibers forming the matrix material are treated, or formed, to be hydrophobic to a certain degree. Traditional methods of forming a nonwoven web comprising the matrix are contemplated (e.g., as described in U.S. Patent App. Pub. no. 20140170402), in addition to other methods such as, for example, electrospinning using fibers formed of all or a portion of hybrophobic fibers or formed another way. In certain embodiments, a batch of untreated fibers is mixed with a batch of pre-treated hydrophobic fibers to create the nonwoven matrix. The ratio of untreated versus pre-treated fibers may vary, for example at a 50/50 ratio. Ratios of between 90/10 (untreated/pre-treated) to 10/90 (untreated/pre-treated) are also contemplated.

In certain embodiments, the treated matrix material is prepared and after preparation holes (e.g., perforations as discussed herein) are introduced though the treated matrix material to enhance dissolution/dispersion and/or decrease sinking and dispersion timing. The holes can be introduced by any known means, including clean-cut and sealed-cut methods. A clean-cut refers to a cut such that the cut may be introduced through individual fibers, thus exposing the internal and untreated surfaces (i.e., surfaces not containing the coating/lamination solution) of the cut area to the environment. A sealed-cut refers to a cut such that the cut may be introduced through individual fibers, but the cut surface is sealed such that the internal surfaces of the fibers are not exposed to the environment, for example, since they are covered with the coating/lamination solution, heat-sealed, etc. Conventional cutting methods are contemplated, including mechanical cutting via die cutting or otherwise with a sharpened instrument in addition to heat-, light-, and/or chemical-based cutting methods. Debossing may also be employed, wherein patterns are introduced to the surface of the matrix material in certain areas (e.g., through a press or another method or means) to provide an aesthetic texture, decrease hydrophobicity by introducing a perforation or hole, and increase dispersion potential in the areas of the material that have been debossed.

As noted, a binding agent forms a component of the exemplary coating/lamination solutions described herein. Starch is the most frequent binding agent, though other water soluble polymers may be employed. Any of a variety of carbohydrate types or water soluble polymers, such as soluble carbohydrates including starch types may be employed. Various concentrations of carbohydrate or other water soluble polymer may be employed in the presently described lamination solutions, including up to about 75% carbohydrate when a hydrophobic nanoparticle is included according to the present methods and solutions. Including higher concentrations of carbohydrate affects the stiffness, reagent binding, and/or dispersion characteristics of the resulting treated matrix material.

The matrix material may be processed independently of the treatment with a hydrophobic nanoparticle to permit its use for any of a variety of purposes. In such embodiments the matrix may also or additionally be treated with a hydrophobic nanoparticle. In such embodiments, the matrix material may be provided in a roll-to-roll web format, where a web of matrix material is advanced through multiple processing stations and wound up on a reel/spool. One exemplary station, or set of stations, includes a buffer/conjugate/reagent application station that, for example, uses pumps (e.g., syringe pumps or another mechanism to provide a measured volume of fluid) and one or more dispenser heads (e.g., two, three, four, 5, or more dispensers) to introduce a predetermined volume of liquid to the matrix material. Multiple spatially-separated dispensers often permits the introduction of a sufficient volume of liquid to the matrix across the necessary area to ease absorption and reduce reagent losses and unintended spreading of the liquid within the matrix. Another exemplary station, or set of stations, includes a test line/control line/reagent station that, for example, uses pumps (e.g., syringe pumps or another mechanism to provide a measured volume of fluid) and one or more dispenser heads (e.g., two, three, four, 5, or more dispensers) to introduce a predetermined volume of liquid to the matrix material. Another exemplary station, or set of stations, includes a drying station comprising one or more (one, two, three, four, or more) dryers such as dry towers, microwave dryers, infrared dryers, or the like. A drying station may be included after either or both of the reagent dispensing stations. In certain embodiments the matrix material is pre-shaped or pre-cut to match its intended purpose prior to advancing through one or more of the processing stations. A similar process may be provided in batch format as well, where each processing station may be integrated or separated and the matrix material is moved in pieces from one processing station to the next.

In certain embodiments, a ligand, binding partner, or conjugate pair member (e.g., streptavidin, avidin, biotin, guteraldehyde), is utilized to deposit a reagent on the matrix. For example, streptavidin or avidin is deposited on the matrix and a biotinylated (or other binding member pair) target specific reagent such as an antibody is applied or introduced to the position on the matrix where the avidin or streptavidin is deposited. In such embodiments, for example, the first binding partner member is deposited and dried, affixed, or otherwise established in place on the matrix in a specific position (e.g., a reagent line, test line, control line, etc.). Thereafter, the biotinylated reagent is introduced to the other member of the binding pair that is held in the matrix. In such embodiments often a highly defined test or control line is established, thus reducing the spread of the target specific reagent across a wider portion of the matrix. In addition to biotin and avidin or streptavidin, other binding components include, as examples without limitation, gluteraldehyde, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), metals and their chelators, and the like. Furthermore, binding components can include members that are analogs of the original binding component member, for example an analyte-analog or a binding component member made by recombinant techniques or molecular engineering. In one exemplary embodiment, the matrix materials is striped at 3 mg/ml streptavidin. The matrix is dried or permitted to dry. Then the streptavidin striped matrix material is striped again with biotynylated antibody (GAMC, PabT, etc.). In another exemplary embodiment, an antibody is reacted with gluteraldehyde and then striped on a matrix material.

Also in certain embodiments, reagents are deposited to the matrix using inkjet or aerosol printing technology. This technology may be utilized in one or more of the processing stations discussed herein. For example, an ink-jet type printer such as the Dimatix Materials Printer (DMP-2850; Fujifilm, Santa Clara, Calif.), an EPSON Stylus C88+, or the like, is employed to deposit a reagent such as an antibody to the matrix material. Test and control lines may be deposited in this matter individually or concurrently. The reagents may be separately immobilized (e.g., photo-immobilization) after printing. In certain embodiments, reagents conjugated with a member of a binding pair, as discussed above, are printed and immobilized to a previously deposited (optionally using inkjet printing) opposite member of the binding pair.

In certain embodiments a nanocellulose solution is applied to the matrix material. The nanocellulose may be in the form of nanocellulose beads, fibers, nanofilaments, and/or nanocrystals, or the like; often suspended in a liquid solution. Though not wishing to be bound to any particular theory of operation, the nanocellulose solution is applied to a matrix and is absorbed within the fiber matrix of the matrix material such as a nonvoven. The matrx material, in general, will have what is often referred to herein for exemplary purposes as a pore size. In a nonwoven material, the pore size is basically the open area within and between adjacent fibers or groups of fibers. The nanocellulose fibers embed within the pores of the nonwoven matrix to fill the gaps and reduce the overall pore size. The nanocellulose solution may be soluble in a sample such that the nanocellulose fibers or beads will mobilize when sample is applied. Alternatively, the nanocellulose may become bonded after initial application to the matrix material such that it does not immediately solubilize when a sample is applied, but will do so as the nonwoven matrix material disperses.

Often a nanocellulose solution is applied to the matrix material prior to the application of a reagent. In certain embodiments, a reagent is combined with a nanocellulose solution (or nanocellulose beads or fibers) and applied as a single solution. The reduced pore size resulting from the deposition of the nanocellulose provides a reduced area for the reagent to bind, dry, or otherwise become retained within the matrix. In such embodiments the reagent is confined to an area or region of the matrix material that is reduced relative to a portion of the matrix material that is untreated. More precise reagent deposition is thereby provided, and often reagent volumes and/or concentrations maybe reduced.

In certain embodiments involving a matrix that requires treatment with a reagent to provide a specific function or ability (e.g., a matrix for use in an assay, a matrix for use to provide an indication, a matrix for use to provide a function, etc.) that is confined to a specific area, the matrix may be treated with a hydrophobic coating, often in a reduced concentration or volume relative to matrix that is not treated with a reagent to provide a specific function or ability yet is treated with a hydrophobic coating. In such embodiments, inkjet or aerosol printing technology is often employed to provide such a coating. In such embodiments, an application of the hydrophobic nanoparticle is provided to the matrix material and permitted to penetrate at least a portion of the matrix material (e.g., 20% to about 80%; most frequently about 40% to 60%, or about 50%). This process provides what is referred to herein as a temporary membrane backing (or simply a membrane backing) for the matrix material. The backing is temporary in that it provides temporary hydrophobicity, as discussed herein, to the matrix material at the location of treatment). Thereafter, a reagent (such as those described herein) is introduced to the hydrophobic coating pre-treated matrix material. In certain embodiments, a target-specific reagent, a ligand reagent, a control reagent, a buffer, or other reagent for purposes of a diagnostic assay is contacted with the matrix material after hydrophobic coating pre-treating of the matrix material.

In certain frequent embodiments, the matrix material (e.g., comprising a web of non-woven matrix material) is coated on one side with a hydrophobic nanoparticle coating, and on the other side the matrix material is left untreated or is treated or includes a reagent such as diagnostic or target specific reagent. In such embodiments, inkjet or aerosol printing technology is often employed to provide such a coating. Often the matrix material is coated with the hydrophobic nanoparticle coating before application of the reagent, and the hydrophobic nanoparticle coating is permitted to dry before applying the reagent. In such embodiments the matrix material is often folded or otherwise manipulated such that the side of the matrix material coated with the hydrophobic nanoparticle lies on the outside of the folded matrix material to act as a housing, with the side including the reagent being internal to the folded matrix material. Stapleless attachment may be utilized to attach the (including one or more) open or free ends of the matrix material to one-another or another device or material. Such embodiments may be co-laminar in physical arrangement or can be provided in any of a variety of 3-dimensional shapes, including papercraft-style ornamental or functional arrangements or shapes. The thus formed matrix may provide a container for something or may be employed in any of a variety of temporal products (including a diagnostic assay). In such embodiments, the hydrophobic nanoparticle coating on the one side of the matrix material often comprises a membrane backing, but is often equally applicable to the additional embodiments described herein. In such arrangements only one side of the matrix material includes the hydrophobic nanoparticle coating and thus has temporary hydrophobicity, but the other side of the matrix material is left untreated (or contains a reduced concentration of a hydrophobic nanoparticle coating) and therefore is not temporarily hydrophobic. When folded or appropriately arranged, water cannot access the hydrophilic (or non-hydrophobic nanoparticle treated) portions of the matrix material. Perforations may be appropriately provided in the matrix material through the hydrophobic coating, as described herein, to ease entry of water past the hydrophobic coating.

Some exemplary coating/lamination solutions are noted below, for example, to be applied to a matrix material. For example, the nonwoven material may be a plurality of layers of HYDRASPUN® (Suominen), SOFTFLUSH® (Jacob Holm & Sons AG), NBOND® (Hangzhou Nbond Nonwoven Co., Ltd. Corp.), or another matrix material. In one embodiment, HYDRASPUN® is 60GSM and fully saturated with coating.

Coating Formulation by Volume:

|  | Solution 1 | Solution 2 | Solution 3 |
| --- | --- | --- | --- |
| Nonwoven material | 2 layers of 80% cellulose, 20% lyocell | 2 layers of 80% cellulose, 20% lyocell | 2 layers of 80% cellulose, 20% lyocell |
| Stiffener Water Nanoparticle Solution | 50% Conc. Starch 10% DI Water 40% hydrophobic nanoparticle solution | 50% Conc. Starch 20% DI Water 30% hydrophobic nanoparticle solution | 50% Conc. Starch 20%-45% DI Water 5%-30% Silicon dioxide (or other hydrophobic nanoparticle) solution |
| Coating add-on weights (dry) | 2 Webs Starch—0.0325 g per square inch hydrophobic nanoparticle solution— 0.0035 g per square inch |  |  |

|  | Solution 4 | Solution 5 | Solution 6 |
| --- | --- | --- | --- |
| Nonwoven material | 2 layers of 80% cellulose, 20% lyocell | 2 layers of 80% cellulose, 20% lyocell | 2 layers of 80% cellulose, 20% lyocell |
| Stiffener Water Nanoparticle Solution | 50% Conc. Starch 10% DI Water 40% hydrophobic nanoparticle solution | 50% Conc. Starch 20% DI Water 30% hydrophobic nanoparticle solution | 50% Conc. Starch 20%-45% DI Water 5%-30% Silicon dioxide (or other hydrophobic nanoparticle) solution |
| Coating add-on weights (dry) | 2 Webs Starch—0.0325 g per square inch hydrophobic nanoparticle solution— 0.0035 g per square inch |  |  |

|  | Solution 7 | Solution 8 | Solution 9 |
| --- | --- | --- | --- |
| Nonwoven material | 12 layer of cellulose nonwoven | 1 layer of cellulose nonwoven | 1 layer of cellulose nonwoven |
| Stiffener Water Nanoparticle Solution | 50% Conc. Starch 10% DI Water 40% hydrophobic nanoparticle solution | 50% Conc. Starch 20% DI Water 30% hydrophobic nanoparticle solution | 50% Conc. Starch 20%-45% DI Water 5%-30% Silicon dioxide (or other hydrophobic nanoparticle) solution |
| Coating add-on weights (dry) | 2 Webs Starch—0.0325 g per square inch hydrophobic nanoparticle solution— 0.0035 g per square inch |  |  |

In the most frequent embodiments, low concentrations of hydrophobic nanoparticles are included in the solution. High concentrations of such hydrophobic nanoparticles can have the opposite of the intended effect and cause floating instead of wetting of a treated matrix material. In this regard, it has been determined that a hydrophobic nanoparticle textile coating or textile shield, if included in flushable embodiments at concentrations equal to or less than 50% of the treatment solution, comfortably passes the sink test for flushability certification. Often, the hydrophobic nanoparticle textile coating or textile shield, if included in flushable embodiments is provided at concentrations of between at or about 15% to at or about 50% of the treatment solution. Also often the concentration is between at or about 30% to at or about 40%. Also often the concentration is between at or about 15% to at or about 40%. Also often the concentration is between at or about 15% to at or about 30%. Also often the concentration is between at or about 15% to at or about 20%. Also often the concentration is between at or about 20% to at or about 30%. Also often the concentration is between at or about 31% to at or about 35%. Also often the concentration is between at or about 40% to at or about 50%. Also in certain embodiments the concentration is between at or below 15% of the treatment solution. The relative concentration of the hydrophobic nanoparticle and the nature of the water dispersible and/or biodegradable matrix material often dictates the volume and concentration of the treatment solution to impart (temporary) hydrophobicity to the matrix material. As such, the hydrophobic nanoparticle textile coating or textile shield, if included in flushable embodiments, may be provided at concentrations of above 50% of the treatment solution if the hydrophobic nanoparticle is provided at a high dilution in the treatment solution. It is also useful to point out that a separate treatment solution may not be needed if the matrix material is otherwise provided with temporary hydrophobicity, for example, via co-extrusion of the matrix material with the hydrophobic nanoparticle, and/or selection of an appropriate water dispersible polymer and production of the matrix, for example, via electrospinning or other polymer based non-woven matrix production means. We have unexpectedly discovered that by utilizing decreased concentrations of the hydrophobic nanoparticle solution, hydrophobicity can be decreased to a point where the lamination is only temporarily hydrophobic, enough to withstand use, and submersion up to 20 minutes (for example), before taking in water and sinking.

Liquid glass or advanced liquid glass technology may also be employed as or in the hydrophobic nanoparticle coating or nanolayer coating. In certain embodiments, the liquid glass cures to form a nanolayer coating that is inert, harmless, environmentally friendly, non-allergenic, and with no toxicity. Additional exemplary nanolayer coatings maybe formed from or contain Coatings 625, 629, 680, 683, 685, 687, 689, 691, 692, 695, 697, 7685, 7689, among others, available from CCM GmbH, Diepenbrioch, Germany.

Dispersibility is highly dependent on the starch concentration of solution. We have unexpectedly discovered that diluting starch to around about 50% of the treatment solution provides a balance between desired stiffness and the ability to disperse in water. For example, the table below depicts dispersibility of laminations using the following solutions:

50% Starch/45% hydrophobic nanoparticle solution/5% deionized water

50% Starch/40% hydrophobic nanoparticle solution/10% deionized water 58.5% Starch/31.5% hydrophobic nanoparticle solution/ 10% deionized water 50% Starch/31.5% hydrophobic nanoparticle solution/ 18.5% deionized water 50% Starch/31.5% hydrophobic nanoparticle solution/ 18.5% deionized water 55% Starch/31.5% hydrophobic nanoparticle solution/ 13.5% deionized water 50 parts starch/23 parts hydrophobic nanoparticle solution/diluted with deionized water We have also observed that lowered concentrations of the hydrophobic nanoparticle solution often increases dispersibility. Dispersibility is also reliant on the amount of starch used. When undiluted, the material may or may not pass the slosh box dispersibility test. But as starch concentration decreases, dispersibility increases.

The present disclosure contemplates a variety of uses of the treated matrix materials. For example, one type of use includes devices for use in various diagnostic applications such as flushable pregnancy tests or housings. In particular, the coating/lamination process and materials are useful in the other devices or products where an environmentally friendly rigid, yet water dispersible or flushable material, is desired. This rigidity, as described elsewhere herein, can be characterized as temporary in that it will remain rigid (or rigid relative to an untreated matrix material of the same type) as long as it is not exposed to a particular fluid (e.g., water) or moisture for a predetermined time or time range and/or at a specified temperature. After such exposure, dissolution or dispersion of the treated matrix material occurs. In the case of a pregnancy test, whether it is a mid-stream or dipstick style test, once it is contacted with urine the dissolution or dispersion process will begin if the urine has begun to penetrate the coating to contact the underlying fibers of the matrix material. Yet, after this initial contact the device remains to be rigid for a period of time. This process continues and is enhanced when the device is tossed in, for example, the toilet for disposal. Additional non-limiting example uses and devices are contemplated and though a few options are listed, this is not intended to be an exhaustive list. Pet waste scoops, formed packaging, flushable instructions, flushable tampon applicators, among many other uses are contemplated for laminated matrix materials contemplated herein.

Coating materials naturally soluble in water that are useful in the present devices and methods are preferably soluble, for example, after exposure to fluid such as water for a period of time. In certain embodiments, the contact period pushing solubility and dissolution is about up to 10 minutes. In certain embodiments, the contact period pushing solubility and dissolution is between about 5 to 10 minutes. In certain embodiments, the contact period pushing solubility and dissolution is between about 1 to 10 minutes. In certain embodiments, the contact period pushing solubility and dissolution is between about 1 to 5 minutes.

In certain embodiments, a excipient (e.g., water, an acid, a base, a salt, an alcohol, an esther, an ether, a polymer, a lipid, etc.), may be contacted, provided, or utilized to enhance or speed dissolution, water dispersion or biodegradation of materials of the devices contemplated herein ("a dissolution or dispersion excipient"). The dissolution or dispersion excipient may be in liquid, solid, powder, granular, gaseous, or other form. As such, the dissolution or dispersion excipient may be a dissolution or dispersion agent suspended or dissolved in a fluid such as a liquid. In certain embodiments, a dissolution or dispersion excipient is embedded in a fiber (including multiple fibers) of the matrix, included as a component of the matrix material, embedded in the matrix material, or otherwise incorporated in the matrix material. Also often, a dissolution or dispersion excipient is provided separate from the matrix material and is contacted with the matrix material prior to or concurrent with the contact of the matrix material at the time of disposal. In certain embodiments, a dissolution or dispersion excipient is provided in a releasable manner in or with a device comprised of the water dispersible and/or biodegradable matrix material.

In certain embodiments, the matrix material becomes water dispersible, flushable, biodegradable, and/or compostable after the addition of a dissolution or dispersion excipient. In such embodiments, less frequently the matrix material is not water dispersible, flushable, biodegradable, and/or compostable until it has contacted (and begun reacting, or reacted) with a dissolution or dispersion excipient.

In certain embodiments, shelf-life determinations, predictions and decisions are made using techniques known in the art, for example those detailed in Woo et al., "Shelf-Life Prediction Methods and Applications," Med. Plastics & Biomat. Mag. (March 1996). In certain embodiments, the pH of the coating/lamination solution is adjusted to enhance shelf-life of treated matrix materials. For example, often the pH of the coating/lamination solution is adjusted to be acidic, for example, at a pH of about 3-5. Other methods of enhancing shelf-life may also be employed with the frequent proviso that they do not interfere with dissolution/dispersion characteristics of treated matrix materials, for example by increasing dissolution/dispersion times or significantly increasing such times. When the matrix material is to be utilized in an assay such as a diagnostic assay, such methods of enhancing shelf-life are chosen such that they are inert in, or otherwise do not interfere with, the assay.

Coatings and treatments are also often formulated for specific performance characteristics, such as dissolution rate, viscosity, layer thickness, and porosity, based on desired application. For example, a coating is often chosen based on its bonding with, adherence to, or integration within, the matrix material. A coating is also often chosen to provide for a predetermined dissolution rate based on the analyte of interest, user type, analyte identification sensitivity desired, among other reasons.

Treated matrix materials of the present disclosure are provided in a variety of configurations and layouts, and/or for a non-limited variety of uses and purposes. The presently described materials and methods provide for the creation of a variety of what is referred to herein as temporary or temporal products. These are products that have the structural integrity of, for example, a plastic molded product, frame or housing. Yet when these temporal products are exposed to water or another natural or environmental stimulus (with or without a dissolution or dispersion excipient) for a certain duration of time and the underlying matrix material becomes wetted, they soften and may be disposed of in an environmentally friendly manner such as disposal in a toilet or as compost. Such products are often water dispersible and/or biodegradable. In such products, the matrix material is employed together with the use of a temporary hydrophobic coating, such as coatings described herein including a hydrophobic nanoparticle.

Some examples of temporal products include packaging, wound dressings, diagnostics (human, vetrinary), pet product consumables, hospital and/or environmental facilities products, potty training accessories, temporary structures, among others. Some examples of packaging include plastic cassette casings, cardboard replacement, plastic replacements, etc. Some examples of diagnostics include lateral flow, vertical flow, and dipstick diagnostics, puppy pee pad diagnostics, kitty litter box, kitty litter (see pretty litter), etc. Some examples of pet product consumables include scoops for waste collection and waste or training pads; water bowls for on the go (foldable, disposable, etc.); cage, carrier liners; cleaning scrub brush/hand glove that contains soap; etc. Some examples of hospital and/or environmental facilities products include laundry bags, urinal cakes, bed pans, bed pads, hospital masks, disposable sanitary filters, HVAC filters, HEPA filters, and infection prevention wraps, protectors and/or coverings for equipment, etc. Some examples of potty training accessories include potty training toilet inserts. Some examples of temporary structures include porta potties, baby pools, outdoor seating, etc.

Certain advantages are provided with the currently described materials, methods, and devices. In particular, the device (i.e., assay/test strip/testing device) is dispersible or soluble in water. Most frequently, the device is biodegradable. Fewer components and fewer materials are needed to manufacture and functionally utilize the device according to any desired assay, which permits component integration and eases manufacturing complexities.

The above examples are included for illustrative purposes only and are not intended to limit the scope of the disclosure. Many variations to those methods, systems, and devices described above are possible. Since modifications and variations to the examples described above will be apparent to those of skill in this art, it is intended that this invention be limited only by the scope of the appended claims.

One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety and/or for the specific reason for which they are cited herein.

We claim:

1. A treated water dispersible and/or biodegradable matrix material comprising a binding agent and a hydrophobic nanoparticle coating, wherein the hydrophobic nanoparticles penetrate at least a portion of the matrix material, and wherein a dry treated matrix material is woven or nonwoven web material and is rigid such that it is formable and can be manipulated to form a three-dimensional shape when wetted and this shape is resistant to deformation when dried, and wherein the matrix material is arranged in a 3-dimensional shape.

2. The treated matrix material of claim 1, wherein the matrix material is comprised of a plurality of fibers and at least one of the plurality of fibers is coated with the binding agent and the hydrophobic nanoparticle coating.

3. The treated matrix material of claim 1, wherein the treated matrix material comprises a water dispersible and/or biodegradable cellulosic nonwoven web, or a water dispersible and/or a biodegradable nonwoven matrix material comprised of electrospun fibers.

4. The treated matrix material of claim 1, wherein the matrix material comprises multiple layers, and wherein each layer of the multiple layers is attached to another layer of the multiple layers using stapleless attachment.

5. The treated matrix material of claim 1, wherein the matrix material is water dispersible and the binding agent comprises a starch.

6. The treated matrix material of claim 1, wherein the hydrophobic nanoparticle comprises non-fluorinated silicon dioxide.

7. The treated matrix material of claim 1, wherein the matrix material comprises a sheet of material having two sides, and wherein the hydrophobic nanoparticles penetrate at least a portion of the matrix material to provide a temporary membrane backing one side of the matrix material, and wherein the reagent is applied to the side of the matrix material opposite the temporary membrane backing.

8. The treated matrix material of claim 6, wherein the matrix material is comprised in a diagnostic device adapted to conduct a diagnostic assay by the inclusion of a reagent to provide a specific function or ability, wherein the reagent is a target-specific diagnostic reagent, a ligand diagnostic reagent, and/or a diagnostic control reagent.

9. The treated matrix material of claim 1, wherein the treated matrix material is temporarily rigid and remains rigid after exposure to water for over one minute.

10. The treated matrix material of claim 1, wherein the treated matrix material is temporarily rigid and adapted to remain rigid after exposure to water for a predetermined time.

11. The treated matrix material of claim 10, wherein the predetermined time is between 1 to 10 minutes.

12. The treated matrix material of claim 1, wherein the binder comprises nanocellulose.

13. A treated water dispersible matrix material comprising a binding agent and a hydrophobic nanoparticle coating, wherein the hydrophobic nanoparticles penetrate at least a portion of the matrix material, and wherein a dry coated matrix material is rigid, wherein the matrix material is comprised in a diagnostic device adapted to conduct a diagnostic assay by the inclusion of a reagent to provide a specific function of ability, wherein the reagent is a target-specific diagnostic reagent, a ligand diagnostic reagent, and/or a diagnostic control reagent, and wherein the treated matrix material is temporarily rigid and adapted to remain rigid after exposure to water for a predetermined period of time.

14. The treated matrix material of claim 13, wherein the predetermined time is between 1 to 10 minutes.

15. The treated matrix material of claim 13, wherein the predetermined time is over one minute.

* * * * *